United States Patent [19]

Braid

[11] 4,198,303

[45] Apr. 15, 1980

[54] ANTIOXIDANT LUBRICANT COMPOSITIONS

[75] Inventor: Milton Braid, Westmont, N.J.

[73] Assignee: Mobil Oil Corporation, New York, N.Y.

[21] Appl. No.: 901,938

[22] Filed: May 1, 1978

[51] Int. Cl.$^2$ .................. C10M 1/54; C07F 15/04
[52] U.S. Cl. .................. 252/42.7; 44/68;
 252/46.4; 252/49.7; 260/45.75 N; 260/429 D; 260/439 R
[58] Field of Search .................. 252/42.7, 46.4, 49.7; 260/45.75 N, 429 D, 439 R; 44/68

[56] References Cited

U.S. PATENT DOCUMENTS

| | | | |
|---|---|---|---|
| 2,342,099 | 2/1944 | Ashley et al. | 260/429 D X |
| 2,362,293 | 11/1944 | McNab et al. | 260/429 D X |
| 2,380,299 | 7/1945 | Evans et al. | 260/429 D X |
| 2,409,687 | 10/1946 | Rogers et al. | 260/429 D |
| 2,449,026 | 9/1948 | Van Gilder | 260/429 D X |
| 2,703,786 | 3/1955 | Young et al. | 252/42.7 |
| 3,006,885 | 10/1961 | Dickson, Jr. | 260/45.75 N |
| 3,210,277 | 10/1965 | Swift | 252/42.7 |
| 3,313,770 | 4/1967 | Foster | 260/45.75 N |
| 3,390,160 | 6/1968 | Heller et al. | 260/429 D |
| 3,632,825 | 1/1972 | Jordan | 260/45.75 N X |
| 3,636,022 | 1/1972 | Bright | 260/45.75 N X |
| 3,636,023 | 1/1972 | Murray et al. | 260/439 R |
| 3,975,358 | 8/1976 | Stretanski | 260/45.75 N |
| 4,013,620 | 3/1977 | Henderson, Jr. et al. | 260/45.75 N X |
| 4,025,488 | 5/1977 | Dix et al. | 260/45.75 N |
| 4,026,866 | 5/1977 | Rasberger et al. | 260/45.75 N |
| 4,119,548 | 10/1978 | Braid | 260/439 R X |
| 4,151,100 | 4/1979 | Braid | 252/42.7 |

*Primary Examiner*—Thomas A. Waltz
*Attorney, Agent, or Firm*—Charles A. Huggett; Raymond W. Barclay; Howard M. Flournoy

[57] ABSTRACT

Nickel thiobis(alkylphenolates), e.g., nickel 2,2'-thiobis-(4-t-octylphenolate), complexed with hydroxy materials such as alcohols and phenols are novel compounds which impart antioxidant properties to various organic media such as lubricants, hydrocarbon fuels and plastics when incorporated therein. Synergistic or improved antioxidant compositions are provided when the hydroxy complexes are admixed with known antioxidants such as aryl amines and/or hindered phenols.

46 Claims, No Drawings

ANTIOXIDANT LUBRICANT COMPOSITIONS

BACKGROUND OF THE INVENTION

1. Field of the Invention

This invention relates to nickel (II) thiobis-(alkylphenolates) complexed with hydroxyl-substituted ligands such as alcohols and phenols as novel compounds and to organic compositions, normally subject to oxidative degradation such as lubricants and plastics, containing a minor amount of said nickel thiobis(alkylphenolate) complex sufficient to impart antioxidant and ultraviolet stabilization thereto.

Another aspect of this invention is directed to compositions containing the above-referred to novel complexes in which the compositions comprise said complexes and an organic medium selected from oils of lubricating viscosity or greases prepared therefrom, said oils may be hydrocracked lubricating oils, hydraulic oils, automotive oils, gear oils, or transmission fluids, waxes, liquid hydrocarbon fuels, and distillate fuel oils wherein said oils may be mineral oils or fractions thereof or synthetic hydrocarbon base oils. The additive compounds cited hereinabove are also useful for stabilizing plastics e.g. polyolefins against thermally or light catalyzed oxidative degradation. These fluids normally require the presence of stabilizing agents to inhibit oxidative degradation catalyzed inter alia by ultraviolet light, the presence of metals or resulting from high temperature and other high energy conditions.

2. Description of the Prior Art

The production of lubricant compositions, for example, lubricating oils produced by hydrocracking provides a relatively high viscosity index oil and permits the use of base stocks that would be unsuitable for other purposes. On the other hand, however, hydrocracked lubricating oils tend toward poor stability against ultraviolet light degradation, rapidly forming suspended and/or precipitated insoluble material on exposure to ultraviolet light, such as sunlight, or other sources of actinic radiation. Additionally lubricants may be subjected to high temperatures which tend as mentioned heretofore to catalyze oxidative degradation.

Commercially available ultraviolet stabilizers are listed by class and function and identified as to structure in the Kirk-Othmer Encyclopedia in "Encyclopedia of Chemical Technology"; Second Edition, Vol. 21, pp. 115-122. U.S. Pat. No. 3,832,304 discloses the use of aromatic azo compounds for stabilizing hydrocracked oils. U.S. Pat. Nos. 2,703,786; 2,716,090 and 3,210,277 disclose the use of polyvalent metal, e.g., Ni salts of thiobis(alkylphenols) as oxidation inhibitors and plasticizing agents. Nickel thiobis-(4-t-octylphenolate) is disclosed in U.S. Pat. No. 2,971,940 as a stabilizer for plastics and complexes thereof with amines, e.g., n-butylamine are disclosed in U.S. Pat. No. 3,215,717 as plastic stabilizers. However, there are believed to be no disclosures of these compounds in oils and lubricants. Further none of the foregoing disclosures are directed to organic compositions containing the organo-sulfur-nickel complexes described in accordance with this invention. The subject complexes with hydroxy-substituted ligands are not disclosed by any prior art known to applicant. Accordingly, their use in various compositions comprising organic media such as oils of lubricant viscosity and plastics to impart resistance to oxidation and other induced degradation is also believed to be novel. Therefore, their combination with co-antioxidants such as diarylamines, phenothiazines, etc. is synergistic in controlling oxidation, shows a remarkable degree of improvement at low total additive concentrations, and/or has unusual effectiveness in controlling the formation of sludges commonly observed in the use of such co-antioxidants is also believed to be novel. They are especially useful in imparting protection to lubricant base stocks, e.g. paraffinic hydrocarbons, refined petroleum products and synthetic base stock, e.g., ester base stocks.

SUMMARY OF THE INVENTION

This application is based on the discovery that novel coordination complexes of Ni thiobis(alkylphenolates) with hydroxy-substituted ligands comprise or constitute novel compounds having antioxidant characteristics superior to the nickel thiobis (alkylphenolates) of the prior art, e.g., U.S. Pat. No. 2,971,940, or the nickel thiobis(alkylphenolates) complexes with amino-substituted ligands, e.g., U.S. Pat. No. 3,219,717. These novel compounds also possess superior UV stabilization and energy quenching characteristics, and form synergistic or improved antioxidant combinations or systems with co-additives such as diarylamines.

This application is also directed to compositions comprising a major proportion of an organic medium normally susceptible to oxidative degradation and a minor amount sufficient to impart antioxidant properties and/or ultraviolet stabilization thereto of an organo sulfur-containing nickel complex with a hydroxy organic ligand.

DESCRIPTION OF SPECIFIC EMBODIMENTS

The nickel thiobis(alkylphenolates) useful in this invention have the following general structure

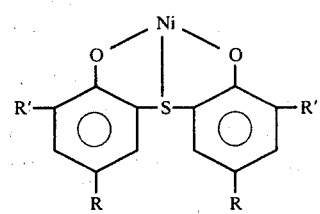

where R is either hydrogen or an alkyl group having from 1 to about 30 carbon atoms. Especially preferred are those compounds having an alkyl group of from 4 to about 16 carbon atoms. Most preferred is an alkyl group having 8 carbons, e.g., 4-t-octyl or 1,1,3,3-tetramethylbutyl. R' is hydrogen or an alkyl group containing from one to about 8 carbon atoms in any isomeric structure except those in which the carbon atom bonded to a ring carbon atom is bonded in turn to more than two other carbon atoms. Preferred is hydrogen, methyl and n-butyl. Most preferred is hydrogen.

The organosulfur-containing complexes of nickel II thiobis (alkylphenolates) and an hydroxy-substituted ligand in accordance with the invention have the following general structure

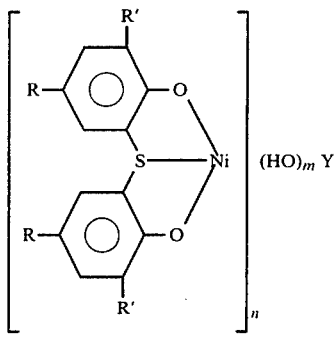

wherein R and R' are as defined above and Y is an alkyl, alkylene, aralkyl, alkaryl or alkylene aryl group having from 1 to about 40 carbon atoms, n is from 1 to 4 and m is from 1 to 6 with the proviso that m is never less than n.

Any suitable hydroxy-substituted ligand may be used to form the coordination complex with the aforementioned nickel thiobis(alkylphenolates). A non-exhaustive list includes methanol, ethanol, propanol, 2-propanol, n-butanol, isobutyl alcohol, benzyl alcohol, 3,5-di-tertiary-butyl-4-hydroxybenzyl alcohol, phenol, 1,4-butanediol, 1,6-hexamethylenediol, 1,8-octamethylenediol, 1,4-cyclohexanedimethanol and the like.

Particularly preferred are alcohols having from 1 to about 4 carbon atoms such as methanol, ethanol, 2-propanol, propanol and butanols; and phenol.

The hydroxy-substituted nickel complexes of this invention may be conveniently prepared by reacting a nickel thiobis(alkylphenol-phenolate) with a suitable hydroxy ligand, e.g., 2-propanol. The reaction mixture is heated to reflux, filtered and the resultant hydroxy-substituted complex recovered (see Example 4). However, the hydroxy-substituted complexes may be also prepared by exchanging or displacing one hydroxy ligand for another. For example a [thiobis(alkylphenolato)]-butanol nickel may be prepared from [thiobis(alkylphenolato)]-2-propanol nickel by displacement of the 2-propanol moiety for a butanol moiety (see Example 6).

The organosulfur-containing hydroxy-substituted nickel complexes in accordance with the invention can be effectively employed in any amount which is sufficient for imparting to the organic medium, e.g., lubricant, the desired degree of protection against oxidative degradation. In many instances, the complex is effectively employed in an amount from about 0.01 to about 5%, by weight, and preferably in an amount from about 0.1 to about 2% by weight, of the total weight of the lubricant composition. As hereinbefore indicated, the novel organic sulfur-containing hydroxy-substituted ligand nickel complexes may be incorporated in any organic media normally subject to oxidative degradation, for example lubricating media which can include oils of lubricating viscosity or greases prepared therefrom in which any of the aforementioned oils or fluids may be employed as vehicles. In general, synthetic oils can also be effectively protected against oxidative and UV degradation. They may also be protected in combination with mineral oils, or as grease vehicles. Typcial synthetic vehicles includes polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxyphenyl)ether, phenoxy phenylether, etc. Generally speaking it is more particularly concerned with areas of lubricating viscosity hydrocarbon fuels and fuel oils which may be mineral oils or fractions thereof or synthetic oils as described hereinabove. With respect to synthetic base stock, ester base stock is preferred.

A non-exhaustive list of suitable arylamine co-antioxidants useful herein are preferably selected from the group consisting of the following: N-phenyl-1-naphthylamine; N-(4'-t-octylphenyl)-1-naphthylamine; N-phenyl-2-naphthylamine; 4,4'-thiobis(N-phenyl-1-naphthylamine); 1,1'-thiobis (N-phenyl-2-naphthylamine); diphenylamine; 4,4'-di-t-octyldiphenylamine; dinaphthylamine; 4-decoxydiphenylamine; phenothiazine. Especially preferred are phenyl naphthylamines such as N-phenyl-1naphthylamine, N-(4-t-octylphenyl)-1-naphthylamine and N-phenyl-2-naphthylamine. However, it is understood that this is a non-limiting list and any arylamine appropriate in view of those disclosed above may be used.

Any suitable hindered phenolic compound may be used herein as a co-antioxidant. Preferred are those selected from the following non-exhaustive list: 2,6-di-t-butyl-p-cresol; 4,4'-methylenebis-(2-6-di-t-butyl-m-cresol); 4,4'-butylidenebis-(6-t-butyl-m-cresol); 4,4'-methylenebis-(2,6-di-t-butylphenol); 2,6-di-t-butylphenol, and 4,4'-butylidenebis-2,6-di-t-butylphenol) 2,4,6-tri-t-butylphenol. Especially preferred is 4,4'-methylenebis-(2,6-di-t-butylphenol).

Generally the weight ratio of nickel complex to arylamine and/or hindered phenol is from about 0.01–5.0 to 1.

The following examples are not meant to be limiting but to merely exemplify the invention as embodied herein.

EXAMPLE 1

Base oil: Table 1—a refined solvent mineral oil characterized by a viscosity of 4.95 Cs at 210° F.

EXAMPLE 2

Nickel 2,2'-thiobis-(4-t-(octylphenolate), (Ni TBP); its method of preparation are described in U.S. Pat. No. 2,971,940.

EXAMPLE 3

[2,2'-thiobis-(4-t-octyl-phenolato)]-n-butylamine Nickel, (NI TBP.C$_4$H$_9$NH$_2$), was obtained commercially. Its method of preparation and structure is described in U.S. Pat. No. 3,215,717.

EXAMPLE 4

[2,2'-thiobis-(4-t-octyl-phenolato)]-2-propanol Nickel (II), NiTBP.i-C$_3$H$_7$OH, was prepared as follows:

One hundred fifty grams of nickel 2,2'-thiobis-(4-t-octylphenolphenolate) (purchased commercially and manufactured in accordance with U.S. Pat. No. 2,971,940), melting range of 147°–149° C., was added to about 650 ml. of 2-propanol. The mixture was then heated while stirring. As the reaction temperature approached 85° C. all of the solids dissolved. After refluxing for about ¼ to ½ hr. solids again began to precipitate. The reaction mixture became progressively more turbid and after 1.5 hr. of refluxing the hot mixture was filtered and the solids collected and dried. 75.7 g. of a light green colored solid with a melting point higher than 300° C. were obtained. Elemental analysis of solids prepared in this way corresponded to the nickel 2,2'-thiobis-(4-t-octylphenolate) complex with 2-propanol [2,2'-thiobis-(4-t-octylphenolato)]-2-propanol nickel II.

Anal. Calcd for $C_{31}H_{98}O_3S$ Ni: C, 66.6; H, 8.7; S, 5.7; Ni, 10.49; Found: C, 65.0; H, 8.5; S, 5.8; Ni, 10.52.

Nickel was determined by thermogravimetric analysis which also established the ratio of one 2-propanol ligand to one nickel thiobis (alkylphenolate) moiety:

Calc'd: % 2-$C_3H_7OH$: 10.74; Found: : 10.59.

EXAMPLE 5

Nickel 2,2'-thiobis-(4-t-butyl-6-methylphenol-phenolate) prepared as described in U.S. Pat. No. 2,971,940 (20 g.) was dissolved in petroleum ether, bp 30°–60° C. As the petroleum ether was allowed to boil off together with some of the alcohol, about 125 ml. of 2-propanol was added to the boiling solution. At the end of the reaction period 50 ml. of 2-propanol was added to bring the reaction mixture back to its original volume. The hot mixture was then filtered to collect the precipitated solids. The complex [2,2'-thiobis-(4-t-butyl-6-methyl-phenolato)]-2-propanol nickel II was then obtained as a light green solid, melting point>300° C.

Anal. Calc'd for $C_{25}H_{36}O_3S$ Ni: S, 6.8; Ni, 12.4; Found: S, 6.9; Ni, 11.8.

EXAMPLE 6

[2,2'-thiobis-(4-t-octylphenolato)]-2-propanol nickel II (83.9 g.) prepared as described in Example 4 was added to 250 g. of 1-butanol and the mixture was heated to reflux, but the 2-propanol complex was mostly insoluble. After refluxing for 1.25 hr. most of the solids had dissolved. A total of 150 ml. of 1-butanol plus 2-propanol was distilled from the mixture and the remainder was filtered to remove solids. From the filtrate upon cooling, there was obtained by collecting the precipitated solids the complex [2,2'-thiobis-(4-t-butyl-phenolato]-1-butanol nickel II, a green solid melting point>300° C.

Anal. Calc'd for $C_{32}H_{50}O_3S$ Ni: C, 67.02; H, 8.79; S, 5.59; Ni, 10.24; Found: C, 66.90; H, 8.79; S, 5.52; N, 9.75.

EXAMPLE 7

[2,2'-thiobis-(4-t-octyl-phenolato)]-ethanol Nickel, Ni-TBP.$C_2H_5OH$ was prepared as follows:

Nickel 2,2'-thiobis-(4-t-octylphenol-phenolate), prepared as in U.S. Pat. No. 2,971,940, (103 g) was dissolved in 450 ml. of petroleum ether by warming to 35° C. The solution was cooled to 25° C. The addition thereto of ethanol was begun as petroleum ether was removed by distillation. The temperature of the reaction mixture was then raised to 50° C. During 1.5 hr. 400 ml. of ethanol were added and 450 ml. of petroleum ether had been removed. The hot reaction mixture was then filtered to collect the solids which had precipitated during the reaction. There was thus obtained 49 g. of the powdery light green complex [2,2'-thiobis-(4-t-octylphenolato)]ethanol nickel II, melting higher than 300° C.

Anal. Calc'd for $C_{30}H_{46}O_3S$ Ni: S, 5.88; Ni, 10.76; Found: S, 6.05; Ni, 10.0.

EXAMPLE 8

[2,2'-thiobis-(4-t-octylphenolato)]-methanol Nickel (II) NiTBP.$CH_3OH$ was prepared as follows:

Nickel 2,2'-thiobis-(4-t-octylphenol-phenolate) prepared as described in U.S. Pat. No. 2,971,940 (103 g) was dissolved in warm petroleum ether, bp. 30°–60° C. (400 ml) and while stirring methanol (10 ml) was added at a rate sufficiently slow as to control the frothing of solvent generated by the resulting exothermic reaction. Additional methanol was then added while the mixture was heated to boil off the petroleum ether until solvent exchange was complete. The green solids which began to precipitate with the first methanol addition increased in amount throughout the reaction period and were collected by filtration of the hot methanolic reaction mixture. The complex [2,2'-thiobis-(4-t-octylphenolato)] methanol nickel II was thus obtained as a light green powdery solid melting higher than 300° C.

EXAMPLE 9

[2,2'-thiobis-(4-t-octyl-phenolato)]-benzyl alcohol Nickel II, NiTBP.$C_6H_5OH$ was prepared as follows: p [2,2'-thiobis-(4-t-octylphenolato)]-2-propanol nickel II prepared as described in Example 4 (83.9 g) was dissolved in benzene (250 ml) and benzyl alcohol (16.2 g) was then added. The resulting solution was heated and refluxed for 1 hr. The displaced 2-propanol and most of the benzene solvent was then removed by distillation and the remainder by rotary evaporation. The complex[2,2'-thiobis-(4-t-octylphenolato)]benzyl alcohol nickel II was thus obtained as a green solid which softened at 150° C., melted partially at 210° C. and was completely fused at 260° C.

Anal. Calc'd for $C_{35}H_{48}O_3S$ Ni: S, 5.3; Ni, 9.7; Found: S, 5.4; Ni, 8.5.

EXAMPLE 10

[2,2'-thiobis-(4-t-octylphenolato)]-2-propanol nickel II (83.9 g) prepared as described in Example 4 was dissolved in benzene (250 ml) and 3,4-di-t-butyl-4-hydroxybenzyl alcohol (35.5 g) was added. The temperature of the mixture was raised to reflux and the resulting solution was refluxed for 2.25 hr. Displaced 2-propanol and benzene (150 ml) were then distilled from the reaction mixture. Remaining solvent was removed by rotary evaporation. From the residue the complex [2,2'-thiobis-(4-t-octylphenolato)]-3,4-di-t-butyl-4-hydroxybenzyl alcohol nickel II was obtained by recrystallization from n-octane as a green solid m.p. 253°–255° C.

Anal. Calc'd for $C_{43}H_{64}O_4S$ Ni: C, 70.20; H, 8.77; S, 4.36; Ni, 7.98; Found: C, 69.94; H, 9.32; S, 3.98; Ni, 7.43.

EXAMPLE 11

[2,2'-thiobis-(4-t-octylphenolato)]-phenol Nickel II as described in Example 4 (28 g) and phenol (60 g) were heated together at 100°–110° C. for several hours. The reaction mixture was then cooled, treated with water and filtered. The solids collected were then washed several times with water to complete removal of unreacted phenol. The complex [2,2'-(4-t-octylphenolato)]-phenol nickel II was obtained as a green solid m.p. higher than 300° C.

EXAMPLE 12

[2,2'-thiobis-(4-t-octylphenolato)]-2-propanol nickel II (83.9 g) prepared as described in Example 4 was dissolved in benzene (250 ml), 1,8-octanediol (22.8 g) was added and the mixture was heated to reflux temperature. The resulting clear solution was refluxed for about 1 hr. and near the end of this period the mixture became cloudy. The reaction mixture was cooled and filtered. The complex bis-[2,2'-thiobis-(4-t-octylphenolato)]-(1,8-octanediol) dinickel II was thus obtained as a green solid melting over the range 136°–145° C.

Anal. Calc'd for $C_{64}H_{98}O_6S_2Ni_2$: C, 67.15; H, 8.63; Found: C, 67.29; H, 9.04.

EXAMPLE 13

[2,2'-thiobis-(4-t-octylphenolato)]-2-propanol nickel II (83.9 g) prepared as described in Example 4 was dissolved in benzene (250 ml) and the solution was heated to reflux temperature. 1,6-hexanediol (8.86 g) was dissolved in the refluxing solution and the reaction mixture was refluxed for about 2 hrs. before displaced 2-propanol and benzene solvent was distilled from the reaction vessel. After 100 ml. of benzene was removed, the reaction mixture was cooled and the solids were collected by filtration. The complex bis-[2-2'-thiobis-(4-t-octylphenolate)]-(1,6-hexanediol) dinickel II was obtained as a green solid melting higher than 300° C.

Anal. Calc'd for $C_{62}H_{94}O_6S_2Ni_2$: C, 66.69; H, 8.48; S, 5.74; Found: C, 68.11; H, 8.25; S, 5.10.

EXAMPLE 14

[2,2'-thiobis-(4-t-octylphenolato)]-2-propanol nickel II (83.9 g) prepared as described in Example 4 was dissolved in benzene (250 ml) and the solution was heated to reflux. To the refluxing solution 1,4-cyclohexanedimethanol (10.8 g) was added. The reaction mixture became progressively more cloudy during the ensuing 2 hr. reflux period. Displaced 2-propanol and benzene (100 ml) were then removed by distillation. The hot reaction mixture was filtered to collect the product complex bis-[2,2'-t-octylphenolato)]-(1,4-cyclohexanedimethanol)dinickel II as a green solid melting higher than 300° C.

Anal. Calc'd for $C_{64}H_{96}O_6S_2Ni_2$: C, 67.27; H, 8.47; S, 5.61; Ni, 10.25; Found: C, 67.13; H, 8.52; S, 5.35; Ni, 9.5.

EXAMPLE 15

A synthetic lubricant comprising a pentaerythritol ester prepared from a mixture of $C_5$ and $C_9$ monocarboxylic acids was prepared as follows:

One group of the above prepared additive complexes (Table 1) was tested in solvent refined mineral oil (Example 1). A second group (Table 2) was tested in the presence of a synthetic lubricant (Example 12) comprising a pentaerythritol ester prepared from a mixture of $C_5$ and $C_9$ monocarboxylic acids. The first group (Table 1) was tested at 325° F. with a 40-hour air treatment and the second group (Table 2) was tested at 450° F. with a 24-hour treatment. The samples are observed for increase in acidity (NN) and kinematic viscosity (KV) after treatment, the loss in weight of the lead specimen and the relative amount of visual sludge. The test procedure is described hereinbelow.

CATALYTIC OXIDATION TEST

A sample of the base lubricant is placed in an oven at a desired temperature. Present in the sample are the following metals either known to catalyze organic oxidation or commonly used materials of construction.

a. 15.6 sq. in. of sand-blasted iron wire,
b. 0.78 sq. in. of polished copper wire,
c. 0.87 sq. in. of polished aluminum wire, and
d. 0.167 sq. in. of polished lead surface.

Dry air is passed through the sample at a rate of about 5 liters per hour.

TABLE 1

CATALYTIC OXIDATION TEST
325° F., 40 HR. MINERAL OIL BASE STOCK

| Additive | Conc. Wt. % | Δ NN | Δ KV % | Lead Metal Loss, mg. | Sludge |
|---|---|---|---|---|---|
| Example 1 (None) | — | 17 | 334 | 66 | Heavy |
| Example 2, NiTBP | 1 | 7.2 | 57 | 1.5 | Moderate |
|  | 0.5 | 6.6 | 41 | 0.7 | Moderate |
|  | 0.25 | 7.3 | 50 | 0.2 | Moderate |
| Example 3, NiTBP . $C_4H_9NH_2$ | 0.5 | 3.7 | 14 | 1.0 | Heavy |
|  | 0.25 | 5.1 | 18 | 1.1 | Heavy |
| Example 4, NiTBP . $i\text{-}C_3H_7OH$ | 0.5 | 4.1 | 42 | 0 | Heavy |
|  | 0.25 | 4.8 | 39 | 0 | Heavy |
| Example 7, NiTBP . $C_2H_5OH$ | 1 | 7.3 | 30 | 0.6 | Heavy |
|  | 0.5 | 3.7 | 16 | 1.3 | Moderate |
|  | 0.25 | 2.96 | 11 | 0.6 | Moderate |
| Example 8, NiTBP . $CH_3OH$ | <0.5 | 2.2 | 16 | 1.6 | Heavy |
| Example 9, NiTBP . $C_6H_5CH_2OH$ | 1 | 4.3 | 48 | 1.1 | Heavy |
|  | 0.5 | 5.9 | 43 | 0.4 | Heavy |
|  | 0.25 | 6.4 | 45 | 0.1 | Heavy |
| Example 10, NiTBP . 3,5 + $(t\text{-}C_4H_9)_2\text{-}4\text{-}OH\text{-}C_6H_2CH_2OH$ | 1 | 6.4 | 46 | — | Heavy |
|  | 0.5 | 6.9 | 44 | 0.2 | Moderate |
|  | 0.25 | 8.4 | 55 | — | Moderate |
| Example 13, $(NiTBP)_2$ . $HO(CH_2)_6OH$ | <1 | 9.3 | 82 | 0.4 | Heavy |

TABLE 1-continued
CATALYTIC OXIDATION TEST
325° F., 40 HR. MINERAL OIL BASE STOCK

| Additive | Conc. Wt. % | Δ NN | Δ KV % | Lead Metal Loss, mg. | Sludge |
|---|---|---|---|---|---|
| Example 4, NiTBP . i-C₃H₇OH + 4,4'-methylenebis (2,6-di-t-butylphenol) | 0.25 / 1 | 3.8 | 25 | — | Heavy |
| Example 4, NiTBP . i-C₃H₇OH + 4,4-di-t-octyl-di-phenylamine' | 0.25 / 1 | 1.4 | 13 | — | Moderate |
| Example 4, NiTBP . i-C₃H₇OH + N-phenyl-1-naphthylamine' | 0.5 / 0.5 | 2.9 | 18 | — | Heavy |
| Example 8, NiTBP . CH₃OH + 4,4'-methylenebis (2,6-di-t-butylphenol) | <0.5 / 1 | 4.5 | 29 | — | Heavy |
| Example 13 + | 1 | | | | |
| N-phenyl-1-naphthylamine | 0.5 | 2.3 | 33 | — | Heavy |
| 4,4'-methylenebis(2,6-di-t-butylphenol) | 2 | 4.6 | 34 | — | Moderate |
| | 1 | 5.2 | 47 | — | Heavy |
| 4,4'-di-t-octyl-di-phenylamine | 2 | 1.3 | 18 | 0.3 | Light |
| N-phenyl-1-naphthylamine 2 | 2 | 0.26 | 31 | 0.2 | Light |

TABLE 2
450° F., 24 HR., PENTAERYTHRITOL ESTERS OF C₅ AND C₉ CARBOXYLIC ACIDS

| Additive | Conc. Wt. % | Δ NN | Δ KV, % | Lead Metal Loss, mg. | Sludge |
|---|---|---|---|---|---|
| Example 8 (Base Oil) | — | 8.25 | 586 | 13.7 | Trace |
| Example 2, NiTBP | 2 | 4.8 | 94 | 0.7 | Nil |
| | 1 | 5.4 | 122 | 0.6 | Nil |
| Example 3, NiTBP—C₄H₉NH₂ | 2 | 6.6 | 107 | 14.7 | Nil |
| | 1 | 8.9 | 127 | 9.6 | Nil |
| Example 4, NiTBP . i-C₃H₇OH | 2 | 4.5 | 60 | 0.9 | Nil |
| | 1 | 5.5 | 94 | 1.8 | Nil |
| Example 7, NiTBP . C₂H₅OH | 2 | 5.1 | 63 | 1.8 | Nil |
| | 1 | 5.4 | 120 | 2.3 | Trace |
| Example 8, NiTBP . CH₃OH | <1 | 4.96 | 277 | 3.1 | Nil |
| Example 9, NiTBP . C₆H₅OH | 1 | 4.8 | 241 | 0 | Nil |
| | 0.5 | 5.3 | 374 | 3.4 | Nil |
| Example 10, NiTBP . 3,5-(t-C₄H₉)₂-4-OHC₆H₂OH | 2 | 4.1 | 298 | 0 | Nil |
| | 1 | 4.1 | 186 | 0 | Nil |
| Example 11, NiTBP . C₆H₅CH₂OH | 2 | 5.9 | 256 | 0 | Nil |
| | 1 | 5.8 | 308 | 0 | Nil |

The data tabulated in Tables 1 and 2 clearly demonstrate the utility of this invention in both mineral and synthetic organic fluids. As noted from the tables, the antioxidant characteristics of the present invention, i.e., novel complexes of nickel (II) thiobis(alkylphenolates) with hydroxy-substituted ligands have proven to be markedly superior in direct comparison with prior art nickel complexes.

While this invention has been described with reference to preferred compositions and components therefor, it will be understood by those skilled in the art that departure from the preferred embodiments can be effectively made and are within the scope of the specification.

What is claimed is:

1. An organosulfur-containing complex comprising a nickel II thiobis (alkylphenolate) complex with an hydroxy substituted ligand having the following general structure:

$$\left[ \begin{array}{c} \text{structure} \end{array} \right]_n \cdot (HO)_m Y$$

where R is either hydrogen or an alkyl group having from 1 to about 30 carbon atoms, R' is hydrogen or an alkyl group containing from 1–8 carbon atoms in any isomeric configuration except those in which a carbon atoms bonded to a ring carbon atom is in turn bonded to more than two other carbon atoms, Y is a ligand such that Y (OH) is methanol, ethanol, n-propanol, i-propanol, n-butanol, i-butanol, benzyl alcohol, 3,5-ditertiary-butyl-4-hydroxybenzyl alcohol, phenol, 1,4-butanediol, 1,6-hexamethylenediol, 1,8-octamethylenediol, and 1,4-cyclohexanedimethanol and n is from 1 to 4 and m is from 1 to 6 with the proviso that m is never less than n.

2. The complex of claim 1 in which the nickel thiobis (alkylphenolate) has the following general structure:

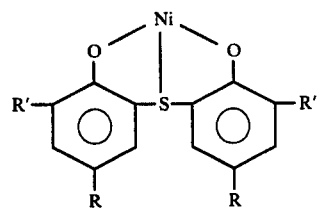

wherein R is either hydrogen or an alkyl group having from 1 to about 30 carbon atoms and R' is hydrogen.

3. The complex of claim 2 in which each alkyl group thereof has from 4 to about 16 carbon atoms.

4. The complex of claim 3 in which each alkyl group contains 8 carbon atoms.

5. The complex of claim 4 in which each alkyl group is a 4-t-octyl radical.

6. The complex of claim 4 in which each alkyl group is 1,1,3,3-tetramethylbutyl.

7. The complex of claim 1 in which the hydroxy-substituted ligand is an alcohol having from 1 to about 4 carbon atoms.

8. The complex of claim 7 in which the alcohol is methanol.

9. The complex of claim 7 in which the alcohol is ethanol.

10. The complex of claim 7 in which the alcohol is propanol.

11. The complex of claim 10 in which the alcohol is 2-propanol.

12. The complex of claim 7 in which the alcohol is a butanol.

13. The complex of claim 1 in which the hydroxy substituted ligand is phenol.

14. The complex of claim 1 in which the hydroxy-substituted ligand is benzyl alcohol.

15. The complex of claim 1 in which the ligand is 3,5-ditertiarybutyl-4-hydroxybenzyl alcohol.

16. The complex of claim 1 in which the ligand is 1,4-butanediol.

17. The complex of claim 1 is 1,6-hexamethylenediol.

18. The complex of claim 1 is 1,8-octamethylenediol.

19. The complex of claim 1 in which the ligand is 1,4-cyclohexanedimethanol.

20. A composition comprising a major proportion of an organic medium normally susceptible to oxidative degradation in which the organic medium is selected from the group consisting of oils of lubricant viscosity or greases prepared therefrom, said oils maybe hydrocracked oils, hydraulic oils, automative oils, gear oils, transmission fluids, waxes, liquid hydrocarbon fuels, fuel oils, and plastics and wherein said oils maybe mineral oils and fractions thereof or synthetic hydrocarbon base oils, and a minor amount sufficient to impart antioxidant properties and/or ultraviolet stabilization thereof of a nickel organosulfur-containing hydroxy complex as described in claim 1.

21. The composition of claim 20 in which the nickel thiobis (alkylphenolate) has the following structure:

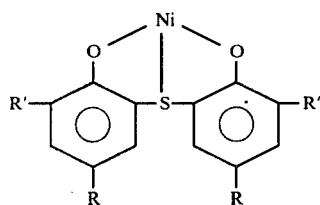

wherein R is either hydrogen or an alkyl group having from 1 to about 30 carbon atoms and R' is hydrogen.

22. The composition of claim 21 in which R is an alkyl group having from 4 to about 16 carbon atoms.

23. The composition of claim 23 in which each alkyl group contains 8 carbon atoms.

24. The composition of claim 23 in which each alkyl group is a 4-t-octyl radical.

25. The composition of claim 23 in which each alkyl group is 1,1,3,3-tetramethylbutyl.

26. The composition of claim 20 in which the hydroxy substituent is an alcohol having from 1 to about 4 carbon atoms.

27. The composition of claim 26 in which the alcohol is methanol.

28. The composition of claim 26 in which the alcohol is ethanol.

29. The composition of claim 26 in which the alcohol is 2-propanol.

30. The composition of claim 23 in which the alcohol is a butanol.

31. The composition of claim 20 in which the hydroxy substituted ligand is benzyl alcohol.

32. The composition of claim 20 in which the hydroxy substituted ligand is 3,5-ditertiary-butyl-4-hydroxybenzyl alcohol.

33. The composition of claim 20 in which the hydroxy substituted ligand is phenol.

34. The composition of claim 20 in which the hydroxy substituted ligand is 1,4-butanediol.

35. The composition of claim 20 in which the hydroxy substituted ligand is 1,6-hexamethylbenediol.

36. The composition of claim 20 in which the hydroxy substituted ligand is 1,8-octamethylenediol.

37. The composition of claim 20 in which the hydroxy substituted ligand is 1,4-cyclohexanedimethanol.

38. A composition according to claim 20 and including an arylamine and/or a hindered phenol.

39. The composition of claim 38 in which the arylamine is selected from N-phenyl-1-naphthylamine; N-(4'-t-octylphenyl)-1-naphthylamine; N-phenyl-2-naphthylamine; 4,4'-thiobis(N-phenyl-1-naphthylamine); 1,1'-thiobis(N-phenyl-2-naphthylamine); diphenylamine; 4,4'-di-t-octyldiphenylamine; dinaphthylamine; 4-decoxydiphenylamine; phenothiazine.

40. The composition of claim 39 in which the arylamine is N-phenyl-1-naphthylamine.

41. The composition of claim 39 in which the arylamine is 4,4-di-t-octyl-diphenylamine.

42. The composition of claim 38 in which the hindered phenol is selected from 2,6-di-t-butyl-p-cresol; 4,4'-methylenebis-(2,6-di-t-butyl-m-cresol); 4,4'-butylidenebis-(6-t-butyl-m-cresol); 4,4'-methylenebis-(2,6-di-t-butylphenol); 2,6-di-t-butylphenol, and 4,4'-butylidenebis-(2,6-di-t-butylphenol) 2,4,6-tri-t-butylphenol.

43. The composition of claim 40 in which the hindered phenol is 4,4'-methylenebis (2,6-di-t-butylphenol).

44. The composition of claim 20 in which the organic medium is an oil of lubricant viscosity.

45. The composition of claim 44 in which the oil of lubricant viscosity is a mineral oil.

46. The composition of claim 44 in which the base oil of lubricant viscosity is a synthetic oil.

* * * * *